United States Patent [19]
Fujiwara et al.

[11] Patent Number: 5,916,874
[45] Date of Patent: Jun. 29, 1999

[54] METHOD FOR TREATING LIVER INJURY

[75] Inventors: Kenji Fujiwara, Oomiya; Satoshi Mochida, Tokyo, both of Japan

[73] Assignee: Asahi Kasei Kogyo Kabushiki Kaisha, Osaka, Japan

[21] Appl. No.: 08/733,564

[22] Filed: Oct. 18, 1996

Related U.S. Application Data

[63] Continuation-in-part of application No. PCT/JP95/00704, Apr. 10, 1995.

[30] Foreign Application Priority Data

Apr. 20, 1994 [JP] Japan .................................. 6-081196

[51] Int. Cl.$^6$ .................................................. A61K 38/00
[52] U.S. Cl. .......................... 514/12; 530/350; 530/380; 530/381
[58] Field of Search ............................. 514/12; 530/350, 530/380, 381

[56] References Cited

FOREIGN PATENT DOCUMENTS

| 0312598 | 4/1989 | European Pat. Off. . |
| 0 474 273 A2 | 11/1992 | European Pat. Off. . |
| 63-132843 | 6/1988 | Japan . |
| 8-231413 | 9/1996 | Japan . |

OTHER PUBLICATIONS

Reeck et al Cell vol. 667, Aug. 1987.
Lewin et al Science 237:1570, 1987.
Zushi et al Journal Bio Chem 266:19886–19889, 1991.
Gomi et al Blood 75(7):1396–1399, 1990.
Robbins et al Pathologic Basis of Disease Third Edition:649–650, 1984.
Fukata Tokyo Jikeikai Medical Journal vol. 110 975–88, Abstract, 1995.
Chazouilleres et al J Gastroenterology and Hepatology vol. 10 471–480, 1995.
Epstein et al Transplantation vol. 54 (1) 12–16, 071992.
Brunetto et al FEMS Microbiological Reviews vol. 14 259–266, 1994.
Gomi, Komakazu, et al., "Antithrombotic Effect of Recombinant Human Thrombomodulin on Thrombin–Induced Thromboembolism in Mice" Blood, vol. 75, No. 7 (Apr. 91) (1990) pp. 1396–1399.
Suzuki, Koji, et. al. "Structure and Expression of Human Thrombomodulin, a Thrombin Receptor in Endothelium Acting as a Cofactor for Protein C Activation", EMBO Journal vol. 6, No. 7, (1987) pp. 1891–1897.
Esmon, Naomi L., et. al., "Isolation of a Membrane–bound Cofactor for Thrombin–catalyzed Activation of Protein C", J. Biol. Chem., 257, pp. 859–864 (1982).
Yamada, S., et. al., "Intravascular Coagulation in the Development of Massive Hepatic Necrosis Induced by *Corynebacterium Parvum* and Endotoxin in Rats", Scand J. Gastroen. erol., 24, pp. 293–298 (1989).
Yasunori Gonda, et. al., "Antithrombotic Efec of Recombinant Human Soluble Thrombomodulin on Endotoxin–induced Disseminated Intravascular Coagulation in Rats", Thrombosis Res., 71, pp. 325–335 (1993).
Michitaka Zuishi, et. al., "Aspartic Acid 349 in the Fourth Epidermal Growth Factor–like Structure of Human Thrombomodulin Plays a Role in its $Ca^{2+}$–Mediated Binding to Protein $C^*$", J. Biol. Chem., 266, 19886–19889 (1991).

*Primary Examiner*—Sheela Huff
*Assistant Examiner*—Julie E Reeves
*Attorney, Agent, or Firm*—Birch, Stewart, Kolasch & Birch, LLP

[57] ABSTRACT

Disclosed is a method for treating liver injury caused by microorganism or toxic substance, which comprises administering to a patient suffering from liver injury a composition comprising a thrombomodulin, which has the ability to bind to thrombin and promote the activation of protein C by thrombin, as an active ingredient and at least one pharmaceutically acceptable carrier. The method of the present invention is very effective for ameliorating liver injury, such as fulminant hepatitis and hepatic veno-occlusive disease (VOD) which is likely to frequently occur after bone marrow transplantation.

4 Claims, 2 Drawing Sheets

100 μm

100 μm

METHOD FOR TREATING LIVER INJURY

This application is a continuation-in-part of PCT Application No. PCT/JP95/00704, filed on Apr. 10, 1995, which designated the United States and on which priority is claimed under 35 U.S.C. § 120.

BACKGROUND OF THE INVENTION

1. Field of the Invention

The present invention relates to a method for treating liver injury. More particularly, the present invention is concerned with a method for treating liver injury, which comprises administering to a patient suffering from liver injury a composition comprising a thrombomodulin as an active ingredient and at least one pharmaceutically acceptable carrier. The method of the present invention is very effective for ameliorating liver injury, such as fulminant hepatitis and hepatic veno-occlusive disease (VOD) which is likely to frequently occur after bone marrow transplantation.

2. Prior Art

Liver is the largest single organ in a living body, and is the principal site of saccharometabolism, protein metabolism and lipid metabolism. In addition, drug metabolism, detoxification, storage of substances, and synthesis of proteins, such as a protein participating in blood coagulation, are also important functions of the liver. Thus, the liver is an essential organ to the maintenance of homeostasis and life. In a physiological view, the above-mentioned functions are the result of individual actions or interactions of the cells which constitute the liver, such as liver parenchyma cells, Kupffer cells and sinusoid endothelial cells. As mentioned above, the liver is an essential organ to a living body. Therefore, once a living body suffers liver injury due to the invasion of a virus from the exterior, the intake of alcohol, or the like, the body is likely to fall into a serious condition.

With respect to liver injury, various causes can be mentioned, for example, toxic substances which directly damage liver parenchyma cells and the metabolism thereof; active oxygen and peroxylipids which are generated during the metabolism of a substance, such as an alcohol; microcirculation injury resulting from a local progress of blood coagulation; and an autoimmunity which is induced by the infection with a hepatitis virus, such as hepatitis B virus.

A number of types of compositions for treating liver injury ascribed to the above-mentioned various causes have been used. However, no therapeutically definitive composition for treating liver injury has yet been developed. This fact is described in detail in the publication, "The Journal of Practical Pharmacy, 41(11) 1–53 (1990)". For example, this publication describes that the majority of parenteral fluids containing amino acids in specific formulations and of vitamin supplements serve only as an auxiliary treatment, such as treatment for supplementing the shortage of essential nutrients and vitamins which is caused by the depression of the metabolisms in liver, and also describes that, with respect to antidotes, representative examples of which include SH compounds, such as glutathione and thiopronine, their detoxification effects are uncertain. Further, according to this publication, various drugs having therapeutic effects against liver injury, such as anti-inflammatory or immunomodulating drugs (e.g., an adrenal cortical hormone, glycylrhizin, azathioprine and the like); protein synthesis accelerators (e.g., malothilate and the like); and interferons having antiviral activity, are known to cause serious side effects, such as hepatic disorder, hypoaldosteronism, agranulocytosis, icterus and cardiomyopathy.

Incidentally, a thrombomodulin is a substance which has the ability to specifically bind to thrombin to inhibit blood coagulation activity of the thrombin, and to promote the activation of protein C by thrombin. Thus, a thrombomodulin is known to have a strong anti-blood coagulation activity. By animal experiments, it has been demonstrated that the thrombomodulin is effective for treatment and prevention of diseases which accompany the progress of blood coagulation, such as thrombosis and disseminated intravascular coagulation (DIC) [see K. Gomi et. al., Blood, 75, 1396–1399 (1990)].

The thrombomodulin is a glycoprotein which is present on the membrane of vascular endothelial cells. Recently, a thrombomodulin is produced by genetic engineering techniques. The cloning of human thrombomodulin cDNA has been reported (see S. Yamamoto et. al, International Application Publication No. WO88/05053), and it has been elucidated that the human thrombomodulin is a membrane-bound protein composed of domain 1 (N-terminal domain), domain 2 (EGF domains), and domain 3 (O-glycosylation site rich domain), wherein domains 1 to 3 are extracellular domains, domain 4 (transmembrane domain) is a hydrophobic region, and domain 5 is an intracellular domain [see The EMBO Journal, 6(7), 1891–1897 (1987)], wherein domains 1 to 5 are arranged in that order starting from the N-terminus thereof. Further, it is known that the minimum active unit of the thrombomodulin is present in the 4th to 6th EGF domains among the six EGF domains constituting domain 2, and that a peptide fragment comprising these 4th to 6th EGF domains of the thrombomodulin is also considered to be effective for the treatment of diseases which accompany the progress of blood coagulation, such as thrombosis and DIC [see M. Zushi et. al., J. Biol. Chem., 266, 19886–19889 (1991)].

However, no reports have been found with respect to the pharmacological effects of a thrombomodulin on diseases other than diseases which accompany the progress of blood coagulation, such as thrombosis and DIC.

SUMMARY OF THE INVENTION

The present inventors have made extensive and intensive studies with a view toward developing a method which is effective for treating liver injury. As a result, it has surprisingly been found that a thrombomodulin, which is known as having the ability to inhibit blood coagulation, is also effective for treating liver injury. Illustratively stated, the present inventors have unexpectedly found that, when a thrombomodulin was experimentally administered to a liver injury model which had been prepared by excising a part of liver from a rat and administering lipopolysaccharide (LPS) to the rat having its liver partly excised, a remarkable improvement was observed in the suppression of the amount of enzymes liberated to serum from the liver, wherein the amount of liberated enzymes is a criterion for liver injury. Further, when the liver tissue of the above-mentioned liver injury model of a rat administered with a thrombomodulin was observed under a light microscope, it was found that the liver injury was remarkably ameliorated. Furthermore, it was found that, when a thrombomodulin was experimentally administered to a mouse liver injury model, which had been prepared by administration with thermally killed microorganisms and LPS, a significant improvement in survival ratio was observed. The above-mentioned liver injury model administered with LPS, or thermally killed microorganisms and LPS, has been regarded as a model which is capable of reproducing a clinical picture of liver injury, especially fulminant hepatitis [see Bioclinica, 9(4), 238–242 (1994)

and Nihon Syokaki Gakkai Zasshi (The Japanese Journal of Gostroenterological Surgery), 83(6), 1161–1167 (1986)]. Further, it was found that, when a thrombomodulin was experimentally administered to a dog hepatic veno-occlusive disease (VOD) model, which had been prepared by administration with monocrotaline, a remarkable improvement in the suppression of the amount of enzymes liberated to serum from the liver and the suppression of the amount of bilirubin in blood was observed, each of which amounts is a criterion for liver injury. The above-mentioned hepatic VOD model administered with monocrotaline has been regarded as a model which is capable of reproducing a clinical picture of liver injury, especially hepatic VOD occurring after bone marrow transplantation [see Transplantation, 54(1), 12–16 (1992)]. The present invention has been completed based on the above findings.

Therefore, it is an object of the present invention to provide a method which is very effective for ameliorating liver injury, such as fulminant hepatitis and hepatic veno-occlusive disease (VOD) which is likely to frequently occur after bone marrow transplantation.

The foregoing and other objects, features and advantages of the present invention will be apparent to those skilled in the art from the following detailed description and appended claims taken in connection with the accompanying sequence listings and drawings.

BRIEF DESCRIPTION OF THE SEQUENCE LISTINGS

In the sequence listings:

SEQ ID NO. 1 is the amino acid sequence which corresponds to the 349th to 462nd amino acids of the entire amino acid sequence of natural human thrombomodulin; and SEQ ID NO. 2 is the amino acid sequence which corresponds to the 1st to 498th amino acids of the entire amino acid sequence of natural human thrombomodulin.

DETAILED DESCRIPTION OF THE INVENTION

Figure 1:
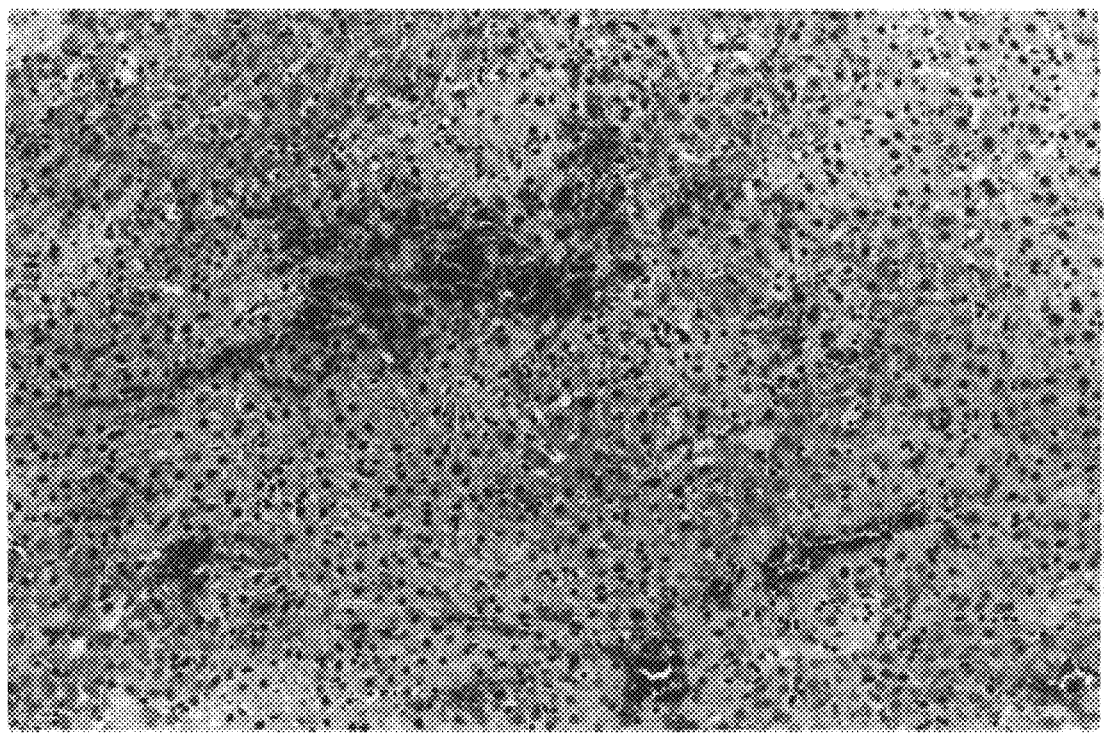
FIG. 1 is a photomicrograph of liver tissue of a rat liver injury model, which was administered with physiological saline in Example 1.

In one aspect of the present invention, there is provided a method for treating liver injury, which comprises administering to a patient having liver injury a composition comprising an effective anti-liver injury amount of a thrombomodulin and at least one pharmaceutically acceptable carrier.

A thrombomodulin which is an active ingredient of the composition used in the present invention is a substance having the ability to bind to thrombin and to promote the activation of protein C by thrombin. Examples of thrombomodulins include human thrombomodulin and a peptide fragment thereof. Preferred are peptides respectively comprising amino acid sequences of SEQ ID NOs. 1 and 2, and homologous variants thereof. Especially preferred are a thrombomodulin consisting of an amino acid sequence of SEQ ID NO. 1 and a thrombomodulin consisting of an amino acid sequence of SEQ ID NO. 2.

A thrombomodulin which lacks domain 4 as the transmembrane domain (hydrophobic domain), such as the above-mentioned thrombomodulin consisting of the amino acid sequence of SEQ ID NO. 1 or 2, is soluble in an aqueous medium without a need for being treated with a surfactant or the like. Therefore, the above-mentioned thrombomodulins respectively having the amino acid sequences of SEQ ID NOs. 1 and 2 can be advantageously used in preparing and using the composition in the present invention, since these thrombomodulins are easy to handle in preparation and use of the composition.

In the present invention, the term "soluble" means that the thrombomodulin can be dissolved in an aqueous medium in a concentration at which a promotion of the thrombin-catalyzed activation of protein C is detected, without a need for the thrombomodulin to be treated with a surfactant. For example, the term "soluble" means that the thrombomodulin can be dissolved, without a need for being treated with a surfactant, in a 20 mM Tris-HCl buffer (pH 7.4) containing 0.1 M sodium chloride, 2.5 mM calcium chloride and 1 mg/ml serum albumin (wherein the buffer has thrombin and protein C added thereto) in a concentration at which a significant promotion of the thrombin-catalyzed activation of protein C is detected (for example, in a concentration of 10 ng/ml or higher). In the present invention, a thrombomodulin having an amino acid sequence other than those of SEQ ID NOs. 1 and 2 can also be preferably used, as long as the thrombomodulin is soluble in an aqueous medium (that is, the thrombomodulin has no transmembrane domain) and has the ability to promote the thrombin-catalyzed activation of protein C.

Also, by treating with a surfactant, natural human thrombomodulin having the entire amino acid sequence of 557 amino acids, containing a transmembrane domain as a hydrophobic domain and an intracellular domain in addition to the extracellular domain, can be rendered usable as the "thrombomodulin" in the present invention.

In the present invention, the term "homologous variant" means a peptide having an amino acid sequence which is obtained by partially changing one of the above-mentioned amino acid sequences by substitution, deletion or the like. The degree of homology between the homologous variant and the original amino acid sequence from which the homologous variant is derived is generally 60% or more, preferably 80% or more, most preferably 90% or more.

The thrombomodulin used in the present invention may contain a sugar residue, such as chondroitin sulfate.

A thrombomodulin can be produced according to a customary method, and reference can be made, for example, to International Application Publication No. WO 88/05053 (S. Yamamoto et al.), J. Biol. Chem., 266, 19886–19889 (1991) (M. Zushi et al.), and J. Biol. Chem., 257, 859–864 (1982) (C. T. Esmon et al.).

In the present invention, the term "liver injury" means not only degeneration or necrosis of liver parenchyma cells which results from injury caused by a certain factor, but also undesirable phenomena caused by biological reactions to the injury, such as mobilization, infiltration, activation of Kupffer cells, leukocytes and the like, fibrosis of the liver tissue, etc., which reactions occur alone or in combination. A "liver injury" can be classified into one of four types, i.e., acute, subacute, chronic and fulminant types, depending on the development of symptoms. Especially noted is fulminant hepatitis, which is one type of liver injury exhibiting symptoms of liver failure (such as disturbance of consciousness) caused by extensive necrosis of liver cells during the course of acute hepatitis. Also noted is hepatic veno-occlusive disease (VOD) which is likely to frequently occur after bone marrow transplantation conducted in the case of chemotherapy or radiation therapy for treating leukemia. Hepatic VOD is a liver injury (the mortality from which is high) which is usually accompanied by an increase in the amount of bilirubin in blood, retention of body fluid, and celiac pain and which, in a histological view, is also accompanied by fibrosis and, in turn, hemorrhagic necrosis of the liver tissue.

The composition used in the present invention for treating liver injury can be obtained as a mixture of an effective anti-liver injury amount of a thrombomodulin with at least one pharmaceutically acceptable carrier. That is, the composition which is suitable for administration to a patient can be prepared by mixing an effective anti-liver injury amount of a thrombomodulin with an appropriate amount of at least one conventional carrier. For example, when the composition is used in the form of an injection, there may be employed as an additive, such as sucrose, glycerol, a pH adjusting agent of various inorganic salts, and the like.

In the method of the present invention, the composition can be administered by a conventional method used for peptide drugs, i.e., parenteral administration, such as intravenous, intramuscular or subcutaneous administration. Alternatively, oral, rectal, nasal or sublingual administration can also be employed.

The dose of the composition varies depending on the age, weight, conditions, etc. of the patient and the manner of administration. In general, however, the dose is about 0.001 to about 20 mg per kg of a patient. The present composition may be administered once a day or, if desired, several times a day.

BEST MODE FOR CARRYING OUT THE INVENTION

Hereinbelow, the present invention will be described in more detail with reference to the following Examples and Comparative Example, but they should not be construed as limiting the scope of the present invention.

EXAMPLE 1

From each of a predetermined number of SD rats (male), about 70% of the liver was excised. 48 Hours after the excision, 200 µg/kg of lipopolysaccharide (LPS) (which had been prepared from $E.$ $coli$ 026: B6 strain manufactured and sold by Difco Laboratories, U.S.A.) and 0.4 ml of a test solution as described below were simultaneously administered to each of the rats through a caudal vein thereof. The above procedure was conducted in accordance with the method of Mochida et al. [Gastroenterology, 99, 771–777 (1990)]. The test solution had been prepared as follows: a thrombomodulin having the amino acid sequence of SEQ ID NO. 2 (hereinafter, frequently referred to simply as "TMD123") was produced in accordance with the method as described in Example 10 and Example 20 of International Patent Application Publication No. WO88/05053 (S. Yamamoto et al.), and two different amounts of the produced TMD123 were individually dissolved in 0.4 ml of physiological saline to prepare two different test solutions, wherein the two different test solutions respectively have concentrations such that, when the two different test solutions were individually administered to SD rats, the amounts of the administered TMD123 became 1 mg and 3 mg per kg of SD rat, respectively.

5 Hours after the administration, a blood sample was taken out from the femoral vein of the rat, and the GPT (glutamic pyruvic transaminase) value of the serum of the blood sample was determined in accordance with the method described in "Rinshou Kensahou Teiyou (Manual of Clinical Testing), 30th edition, p. 656, 1993 (published by Kanehara & Co., Ltd., Japan)".

On the other hand, as controls, male SD rats were individually administered with physiological saline instead of the above test solution, and the GPT values of the respective sera of the rats were determined by the same method as mentioned above.

Results are shown in Table 1.

TABLE 1

|  | GPT value (kU*) average ± standard deviation (SD) |
| --- | --- |
| Rats administered with physiological saline (Number of rats: 11) | 1299 ± 1723 |
| Rats administered with 1 mg/kg of TMD123 (Number of rats: 7) | 244 ± 89 |
| Rats administered with 3 mg/kg of TMD123 (Number of rats: 7) | 184 ± 52 |

*: kilounit

As shown in Table 1, the rats administered with TMD123 had an extremely low GPT value as compared to the rats administered with physiological saline. [As described in Comparative Example 1 below, the serum from the rats administered with heparin (which is known as a substance having the ability to inhibit blood coagulation) showed no significant difference in GPT value from the serum from the rats administered with physiological saline.]

With respect to each of the rats administered with 3 mg/kg of TMD123 and the rats administered with physiological saline, the liver tissue was dyed with hematoxylin and eosin, and the dyed tissue was observed under light microscope (120× magnification).

Figure 2:
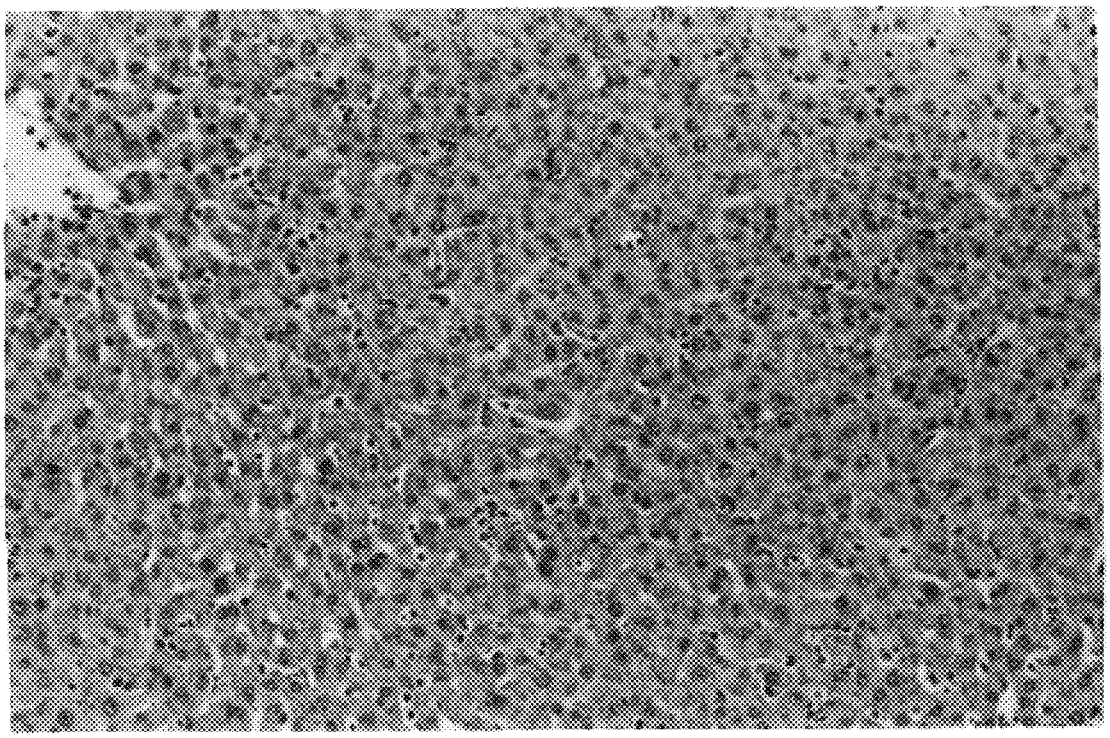
FIG. 2 is a photomicrograph of liver tissue of a rat liver injury model, which was administered with thrombomodulin in Example 1.

The photomicrograph of the liver tissue of the rat administered with physiological saline is shown in FIG. 1, and the photomicrograph of the liver tissue of the rat administered with TMD123 is shown in FIG. 2.

As is seen from FIGS. 1 and 2, with respect to the liver tissue of the rat administered with physiological saline, extensive necrosis of liver cells occurred (FIG. 1), whereas, with respect to the liver tissue of the rat administered with TMD123, no significant difference was observed from normal liver tissue, that is, necrosis of liver cells did not occur (FIG. 2).

From the above results, it can be seen that TMD123 is very useful for treating liver injury.

EXAMPLE 2

Substantially the same procedure as in Example 1 was repeated, except that, in preparing the test solution, a thrombomodulin having the amino acid sequence of SEQ ID NO. 1 (hereinafter, frequently referred to simply as "TME456"), which is described in M. Zushi et al., J. Biol. Chem., 266, 19866–19889 (1991), was used instead of TMD123.

Results are shown in Table 2.

TABLE 2

|  | GPT value (kU*) average ± standard deviation (SD) |
| --- | --- |
| Rats administered with physiological saline (Number of rats: 11) | 1255 ± 1682 |
| Rats administered with 1 mg/kg of TME456 (Number of rats: 7) | 296 ± 95 |
| Rats administered with 3 mg/kg of TME456 (Number of rats: 7) | 216 ± 58 |

*: kilounit

As shown in Table 2, the rats administered with TME456 had an extremely low GPT value as compared to the rats administered with physiological saline. Therefore, it can be seen that TME456 is useful for treating liver injury.

EXAMPLE 3

Lethal models of mice suffering from acute liver failure were obtained in accordance with a partially modified method of the method of Mizoguchi et al. [Journal "Enshou (Inflammation)", 10, 115–118 (1990)]. Illustratively stated, 1 mg (dry weight) of *Propionibacterium acnes* (ATCC 11827) which had been killed by heating was dissolved in 0.2 ml of physiological saline, and the resultant solution was administered to each of male ICR mice through a caudal vein thereof. 7 Days after the administration, a solution of 1 μg of LPS (prepared from *E. coli* 0127: BB strain manufactured and sold by Difco Laboratories, U.S.A.) in 0.1 ml of physiological saline, and a test solution (which had been obtained by dissolving TMD123 in 0.1 ml of physiological saline and had a concentration such that, when the test solution was administered to each of ICR mice, the amount of administered TMD123 became 3 mg per kg of the mouse) were simultaneously administered to each of the male ICR mice through a caudal vein thereof, and a survival ratio was determined 6 hours and 24 hours after the above administration of the LPS solution and the test solution. On the other hand, as controls, male ICR mice, to which physiological saline was administered instead of the above test solution, were tested.

Results are shown in Table 3.

TABLE 3

|  | Survival ratio (%) | |
| --- | --- | --- |
|  | 6 hours after the administration | 24 hours after the administration |
| Rats administered with physiological saline (Number of mice: 20) | 50.0 | 0 |
| Rats administered with TMD123 (Number of mice: 20) | 80.0 | 60.0 |

As shown in Table 3, the mice administered with TMD123 exhibited an extremely high survival ratio, as compared to the mice administered with physiological saline. From the above, it can be seen that TMD123 is very useful for treating liver injury.

EXAMPLE 4

Substantially the same procedure as in Example 3 was repeated, except that, in preparing a test solution, TME456 was used instead of TMD123.

Results are shown in Table 4.

TABLE 4

|  | Survival ratio (%) | |
| --- | --- | --- |
|  | 6 hours after the administration | 24 hours after the administration |
| Rats administered with physiological saline (Number of mice: 20) | 50.0 | 0 |
| Rats administered with TME456 (Number of mice: 20) | 75.0 | 55.0 |

As shown in Table 4, the mice administered with TME456 exhibited an extremely high survival ratio, as compared to the mice administered with physiological saline. From the above, it can be seen that TME456 is very useful for treating liver injury.

EXAMPLE 5

Models of dogs suffering from hepatic veno-occlusive disease (VOD) were obtained in accordance with the method of Epstein et al. [Transplantation, 54(1), 12–16 (1992)]. Illustratively stated, 150 mg/kg of monocrotaline was orally administered to each of male mongrel dogs (weighing 10 to 15 kg) twice per week, wherein the administration was continued for 8 weeks. 4 Weeks after the start of the administration of monocrotaline, administration of two different test solutions (which had been obtained by dissolving two different amounts of TMD123 individually in 0.2 ml of physiological saline and which respectively had concentrations such that, when the two different test solutions were individually administered to mongrel dogs, the amounts of the administered TMD123 became 1 mg and 3 mg per kg of mongrel dog, respectively) to the dogs through a vein thereof once per day was started and continued for 4 weeks. 8 Weeks after the start of administration of monocrotaline, a blood sample was taken out from the vein of the dog, and the GPT value and bilirubin value of the serum of the blood sample was determined by the same method as mentioned above. On the other hand, as controls, male mongrel dogs, to which physiological saline was administered instead of the above test solution, were tested.

Results are shown in Table 5.

TABLE 5

|  | GPT value (kU*) Average ± Standard deviation (SD) | Bilirubin value (mg/dl) average ± standard deviation (SD) |
| --- | --- | --- |
| Dogs administered with physiological saline (Number of dogs: 9) | 1542 ± 1251 | 62.1 ± 35.3 |
| Dogs administered with 1 mg/kg of TMD123 (Number of dogs: 6) | 865 ± 706 | 42.1 ± 21.7 |

TABLE 5-continued

| | GPT value (kU*) Average ± Standard deviation (SD) | Bilirubin value (mg/dl) average ± standard deviation (SD) |
|---|---|---|
| Dogs administered with 3 mg/kg of TMD123 (Number of dogs: 6) | 262 ± 120 | 10.2 ± 4.2 |

*: kilounit

As shown in Table 5, the dogs administered with TMD123 exhibited an extremely low GPT value and an extremely low bilirubin value as compared to the dogs administered with physiological saline. Therefore, it can be seen that a method using TMD123 is very useful for treating liver injury, especially hepatic veno-occlusive disease (VOD).

EXAMPLE 6

Single dose toxicity tests were conducted, each with 5 rats, by administering TMD123 and TME456 individually to the rats (including male and female rats). As a result, it was found that none of the rats died, even when each of TMD123 and TME456 was individually administered in an amount of 180 mg/kg.

COMPARATIVE EXAMPLE 1

Substantially the same procedure as in Example 1 was repeated, except that, as a test solution, a solution of heparin (in the form of sodium salt of heparin, manufactured and sold by The Green Cross Corporation, Japan) in physiological saline (in which the concentration of heparin was adjusted so that, when the test solution was administered to each of the rats, the amount of the administered heparin became 150 U per kg of the rat) was used instead of a solution of TMD123. Heparin is known as a substance having the ability to inhibit blood coagulation.

Results are shown in Table 6.

TABLE 6

| | GPT value (kU*) average ± standard deviation (SD) |
|---|---|
| Rats administered with physiological saline (Number of rats: 7) | 924.3 ± 920.5 |
| Rats administered with heparin (Number of rats: 7) | 754.3 ± 875.7 |

*: kilounit

As shown in Table 6, the serum from each of the rats administered with heparin showed no significant difference in GPT value from the serum from each of the rats administered with physiological saline.

INDUSTRIAL APPLICABILITY

The method of the present invention is very effective for ameliorating liver injury, such as fulminant hepatitis and hepatic veno-occlusive disease (VOD) which is likely to frequently occur after bone marrow transplantation.

We claim:

1. A method for ameliorating liver injury due to fulminant hepatitis or hepatic veno-occlusive disease in a patient which comprises administering to a patient in need thereof an effective amount of thrombomodulin to suppress the serum level of glutamic pyruvic transaminase and bilirubin, wherein said thrombomodulin has the ability to bind to thrombin and promote the activation of protein C by thrombin, and wherein said thrombomodulin is soluble thrombomodulin which lacks a transmembrane domain or which is surfactant-treated thrombomodulin which contains a transmembrane domain.

2. The method according to claim 1, wherein said thrombomodulin consists of the amino acid sequence of SEQ ID NO:1.

3. The method according to claim 1, wherein said thrombomodulin consists of the amino acid sequence of SEQ ID NO:2.

4. The method according to claim 1, wherein said liver injury is due to hepatic veno-occlusive disease.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO: 1:

```
Asp Pro Cys Phe Arg Ala Asn Cys Glu Tyr Gln Cys Gln Pro Leu Asn
1               5                   10                  15

Gln Thr Ser Tyr Leu Cys Val Cys Ala Glu Gly Phe Ala Pro Ile Pro
            20                  25                  30

His Glu Pro His Arg Cys Gln Met Phe Cys Asn Gln Thr Ala Cys Pro
        35                  40                  45

Ala Asp Cys Asp Pro Asn Thr Gln Ala Ser Cys Glu Cys Pro Glu Gly
    50                  55                  60

Tyr Ile Leu Asp Asp Gly Phe Ile Cys Thr Asp Ile Asp Glu Cys Glu
65                  70                  75                  80

Asn Gly Gly Phe Cys Ser Gly Val Cys His Asn Leu Pro Gly Thr Phe
                85                  90                  95
```

```
Glu Cys Ile Cys Gly Pro Asp Ser Ala Leu Val Arg His Ile Gly Thr
                100                 105                 110
Asp Cys (2) INFORMATION FOR SEQ ID NO:2:

(i) SEQUENCE CHARACTERISTICS:
        (A) LENGTH: 498 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO: 2:

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
                20                  25                  30

Ile Cys Asp Gly Leu Arg Gly His Leu Met Thr Val Arg Ser Ser Val
                35                  40                  45

Ala Ala Asp Val Ile Ser Leu Leu Asn Gly Asp Gly Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
                100                 105                 110

Pro Leu Cys Gly Pro Leu Cys Val Ala Val Ser Ala Ala Glu Ala Thr
                115                 120                 125

Val Pro Ser Glu Pro Ile Trp Glu Glu Gln Gln Cys Glu Val Lys Ala
            130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
                180                 185                 190

Ser Ser Ala Ala Val Ala Pro Leu Gly Leu Gln Leu Met Cys Thr Ala
                195                 200                 205

Pro Pro Gly Ala Val Gln Gly His Trp Ala Arg Glu Ala Pro Gly Ala
                210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
                260                 265                 270

Leu Cys Glu His Phe Cys Val Pro Asn Pro Asp Gln Pro Gly Ser Tyr
            275                 280                 285

Ser Cys Met Cys Glu Thr Gly Tyr Arg Leu Ala Ala Asp Gln His Arg
            290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335
```

```
Tyr Asp Leu Val Asp Gly Glu Cys Val Glu Pro Val Asp Pro Cys Phe
            340             345             350

Arg Ala Asn Cys Glu Tyr Gln Cys Gln Pro Leu Asn Gln Thr Ser Tyr
            355             360             365

Leu Cys Val Cys Ala Glu Gly Phe Ala Pro Ile Pro His Glu Pro His
    370             375             380

Arg Cys Gln Met Phe Cys Asn Gln Thr Ala Cys Pro Ala Asp Cys Asp
385             390             395             400

Pro Asn Thr Gln Ala Ser Cys Glu Cys Pro Glu Gly Tyr Ile Leu Asp
            405             410             415

Asp Gly Phe Ile Cys Thr Asp Ile Asp Glu Cys Glu Asn Gly Gly Phe
            420             425             430

Cys Ser Gly Val Cys His Asn Leu Pro Gly Thr Phe Glu Cys Ile Cys
        435             440             445

Gly Pro Asp Ser Ala Leu Val Arg His Ile Gly Thr Asp Cys Asp Ser
    450             455             460

Gly Lys Val Asp Gly Gly Asp Ser Gly Ser Gly Glu Pro Pro Pro Ser
465             470             475             480

Pro Thr Pro Gly Ser Thr Leu Thr Pro Pro Ala Val Gly Leu Val His
            485             490             495

Ser Gly
```